US010858594B2

(12) United States Patent
Ramirez Verduzco et al.

(10) Patent No.: US 10,858,594 B2
(45) Date of Patent: Dec. 8, 2020

(54) HYDRODEOXIGENATION PROCESS OF VEGETABLE OILS FOR OBTAINING GREEN DIESEL

(71) Applicant: INSTITUTO MEXICANO DEL PETROLEO, Mexico City (MX)

(72) Inventors: Luis Felipe Ramirez Verduzco, Mexico City (MX); Jorge Arturo Aburto Anell, Mexico City (MX); Myriam Adela Amezcua Allieri, Mexico City (MX); Maria Del Rosario Socorro Luna Ramirez, Mexico City (MX); Leonardo Diaz Garcia, Mexico City (MX); Blanca Lucia Medellin Rivera, Mexico City (MX); Javier Esteban Rodriguez Rodriguez, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 16/584,544

(22) Filed: Sep. 26, 2019

(65) Prior Publication Data
US 2020/0102506 A1 Apr. 2, 2020

(30) Foreign Application Priority Data

Sep. 27, 2018 (MX) .................... MX/a/2018/011787

(51) Int. Cl.
| | | |
|---|---|---|
| *C10G 3/00* | (2006.01) | |
| *C07C 1/22* | (2006.01) | |
| *C07C 1/207* | (2006.01) | |
| *C10L 1/02* | (2006.01) | |
| *C10L 1/08* | (2006.01) | |

(Continued)

(52) U.S. Cl.
CPC .............. *C10G 3/46* (2013.01); *B01J 21/04* (2013.01); *B01J 21/063* (2013.01); *B01J 23/28* (2013.01); *C07C 1/2076* (2013.01); *C07C 1/2078* (2013.01); *C07C 1/22* (2013.01); *C10G 3/48* (2013.01); *C10G 3/50* (2013.01); *C10G 3/54* (2013.01); *C10L 1/026* (2013.01); *C10L 1/08* (2013.01); *C07C 2521/04* (2013.01); *C07C 2521/06* (2013.01); *C07C 2523/882* (2013.01); *C07C 2523/883* (2013.01); *C10G 2300/1007* (2013.01); *C10G 2300/1014* (2013.01); *C10G 2300/1018* (2013.01); *C10G 2300/202* (2013.01); *C10G 2300/302* (2013.01); *C10G 2300/308* (2013.01); *C10G 2300/70* (2013.01); *C10G 2400/04* (2013.01); *C10G 2400/08* (2013.01); *C10L 2200/0259* (2013.01); *C10L 2200/0263* (2013.01); *C10L 2200/0476* (2013.01); *C10L 2200/0484* (2013.01); *C10L 2270/026* (2013.01); *C10L 2270/04* (2013.01)

(58) Field of Classification Search
CPC ...... C10L 1/08; C10L 1/04; C10L 1/06; C10L 2200/0469; C10L 2270/026; C10L 2270/04; C10L 2200/0484; C07C 1/207; C07C 1/2076; C07C 1/2078; C07C 1/22; C07C 2521/04; C07C 2521/06; C07C 2523/882; C07C 2523/883; B01J 21/04; B01J 21/063; B01J 23/28; C10G 2300/1007; C10G 2300/1014; C10G 2300/1018; C10G 2300/202; C10G 2300/302; C10G 2300/308; C10G 2300/70; C10G 2400/04; C10G 2400/08; C10G 3/46; C10G 3/48; C10G 3/50; C10G 3/54

See application file for complete search history.

(56) References Cited

U.S. PATENT DOCUMENTS

| | | |
|---|---|---|
| 6,383,975 B1 | 5/2002 | Rocha et al. |
| 8,084,655 B2 | 12/2011 | Dindi et al. |

(Continued)

FOREIGN PATENT DOCUMENTS

| | | |
|---|---|---|
| EP | 2540804 A1 | 1/2013 |
| WO | 2015181744 A1 | 12/2015 |

OTHER PUBLICATIONS

Bezergianni | Catalytic Hydroprocessing of Liquid Biomass for Biofuels Production (Chapter 9). Liquid, Gaseous and Solid Biofuels—Conversion Techniques, Prof. Zhen Fang (Ed.), InTech, Mar. 20, 2013.

(Continued)

*Primary Examiner* — Sharon Pregler
(74) *Attorney, Agent, or Firm* — FisherBroyles, LLP; Jason P. Mueller

(57) ABSTRACT

The present disclosure relates to a process for the hydrodeoxygenation of vegetable oils or animal fats to produce green diesel, which comprises contacting the vegetable oil or animal fat with a Nickel-Molybdenum or Cobalt-Molybdenum catalyst supported on alumina-titania or titania, respectively; in a fixed bed reactor in the presence of hydrogen. The process involves hydrocracking, hydrogenation, decarboxylation, decarbonylation, carried out in a fixed bed reactor at temperature of about 270° C. to about 360° C., pressure of about 40 kg/cm² to about 60 kg/cm², liquid hourly space velocity (LHSV) between about 0.8 h⁻¹ to about 3.0 h⁻¹, and H₂/oil ratio of about 2,700 ft³/bbl to about 7,000 ft³/bbl, that allows to obtain a conversion up to 99% and up to 92.7% yield on green diesel.

19 Claims, No Drawings

(51) Int. Cl.
*B01J 23/28* (2006.01)
*B01J 21/06* (2006.01)
*B01J 21/04* (2006.01)

(56) References Cited

U.S. PATENT DOCUMENTS

| | | | |
|---|---|---|---|
| 8,530,715 | B2 | 9/2013 | Strege et al. |
| 8,766,025 | B2 | 7/2014 | Luebke et al. |
| 9,446,998 | B2 * | 9/2016 | Chen .................. C10G 3/44 |
| 2004/0230085 | A1 | 11/2004 | Jakkula et al. |
| 2006/0264684 | A1 | 11/2006 | Petri et al. |
| 2009/0326293 | A1 | 12/2009 | Gomez et al. |
| 2012/0209017 | A1 | 8/2012 | Ouni et al. |
| 2015/0266796 | A1 | 9/2015 | Chen et al. |

OTHER PUBLICATIONS

Kovacs et al. | Fuel production by hydrotreating of triglycerides on NiMo/Al2O3/F catalyst. Chemical Engineering Journal 2011, No. 176-177, pp. 237-243.

Attanatho | Performances and Kinetic Studies of Hydrotreating of Bio-Oils in Microreactor. Ph. D. Thesis. Oregon State University. Aug. 6, 2012.

Sotelo-Boyas et al. | Hydroconversion of Triglycerides into Green Liquid Fuels (Chapter 8). Hydrogenation. Iyad Karam (Ed.), InTech, Oct. 10, 2012.

Furimsky | Hydroprocessing challenges in biofuels production, Review. Catalysis Today 2013, No. 217, pp. 13-56 (abstract).

Bezergianni et al. | Quality and sustainability comparison of one-vs. two-step catalytic hydroprocessing of waste cooking oil. Fuel 2014, No. 118, pp. 300-307.

Mohammada et al. | Overview on the production of paraffin based-biofuels via catalytic hydrodeoxygenation. Renewable and Sustainable Energy Reviews 2013, No. 22, pp. 121-132.

Sinha et al. | Development of Hydroprocessing Route to ransportation Fuels from Non-Edible Plant-Oils. Catal Surv Asia 2013, No. 17, pp. 1-13.

Liu et al. | Hydrotreatment of Jatropha Curcas Oil to Produce Green Diesel Over Trifunctional NiMo/SiO2Al2O3 Catalyst. Chemistry Letters. 2009, vol. 38(6), pp. 552-553.

Nagi et al. | Palm Biodiesel an Alternative Energy for the Energy Demands of the future. 2008, ICCBT F(07), pp. 79-94.

* cited by examiner

HYDRODEOXIGENATION PROCESS OF VEGETABLE OILS FOR OBTAINING GREEN DIESEL

CROSS-REFERENCE TO RELATED APPLICATIONS

This application claims priority to Mexican Patent Application No. MX/a/2018/011787, filed Sep. 27, 2018, the entire contents of which are incorporated herein by reference.

DESCRIPTION

Field of the Disclosure

The present disclosure relates to a hydrodeoxygenation (HDO) process of vegetable oils or animal fats to produce paraffinic hydrocarbons in the diesel range. The HDO reaction is carried out in a fixed bed reactor where a Nickel-Molybdenum-based catalyst is loaded. The green diesel or renewable diesel meets the physical and chemical properties of standards, and it can be used as fuel directly, or mixed with fossil diesel.

Background of the Disclosure

The fuel demand and its concern on carbon fingerprint are rapidly increasing worldwide. This fact has promoted the interest of exploring alternative energy sources to those offered by the fossil fuels that might allow the mitigation of $CO_2$ emissions to the environment.

One alternative might be the use of renewable sources from biomass, such as edible and non-edible vegetable oils (e.g. castor, corn, *Jatropha curcas*, palm, rapessed, soy, etc.) or animal fats (beef tallow, lard, etc.), as well as used cooking oil among others. Those raw materials are composed mainly of triacylglycerides and fatty acids that commonly contain aliphatic chains of 8 to 24 carbon atoms, which could be mono-, di- or poly-unsaturated.

One of the most promising methods to convert vegetable oils and animal fats to liquid fuels is by means of a hydrotreatment process, which converts vegetable oils and animal fats into paraffins, which may be converted to iso-paraffins through isomerization and hydrocracking reactions with the purpose of obtaining advanced aviation fuels.

A catalytic process allows the conversion of triacylglycerides and free-fatty acids into paraffins and iso-paraffins within the range of naphtha, kerosene, and diesel. The products obtained with this process have similar chemical and physical properties as fossil fuels. The biomass conversion is carried out by hydrotreatment at high temperatures and pressures in the presence of catalysts and in an atmosphere of hydrogen. This catalytic process is quite similar to the typical process applied to middle distillate oil streams.

The process comprises a hydrogenation and deoxygenation reaction zone where the HDO of triacylglycerides occurs to produce paraffinic hydrocarbons, propane, and water. Isomerization reactions could be included as an additional stage.

Most of the acylglycerides will be triacylglycerides, but monoacylglycerides, diacylglycerides, and free-fatty acids could be also be presented and likely processed by HDO. At the end of the process, useful hydrocarbons products in the range of diesel, jet fuel, gasoline or naphtha, and propane are obtained, which can used individually or mixed with other compounds.

The hydrotreatment process of vegetable oils or animal fats includes hydrogenation and deoxygenation reactions (e.g. decarboxylation, decarbonylation and deoxygenation reactions), in order to remove the oxygen content of triacylglycerides and thus achieve the production of $H_2O$, $CO$, $CO_2$, as well as paraffinic hydrocarbons. The raw material or feedstock is contacted with a catalyst in the presence of $H_2$ by using operating conditions that promote the hydrogenation of olefins and unsaturated compounds. To improve the quality of the produced biofuel, the hydrotreatment stage could be followed by the isomerization stage in the presence of hydrogen (hydroisomerization) with the main purpose to form iso-paraffins by means of the branching of the previously obtained paraffins.

The HDO of vegetable oils or animal fats could be carried out by using catalysts that are common in the hydrotreatment of oil streams from petroleum industry, such as NiMo, NiW or CoMo catalysts. These types of catalysts are also able to promote the decarbonylation, decarboxylation, and deoxygenation reactions in order to remove the oxygen present in the lipid biomass raw material.

The hydrogenation reactions are carried out at a temperature of about 270° C. to about 360° C., an LHSV from about $0.8\ h^{-1}$ to about $3\ h^{-1}$, and a pressure from about 569 psi to about 996 psi, equivalent to about 40 $kg/cm^2$ to about 60 $kg/cm^2$.

Depending on the type of raw material, the product that is obtained is comparable with the fraction of diesel obtained from fossil fuels, because the product obtained by the HDO of vegetable oils and animal fats contains paraffinic hydrocarbons in the range of about 8 carbon atoms to about 24 carbon atoms, mostly between 15 to 18 carbon atoms. This range of carbon atoms may be desirable when the production of diesel is sought.

From the above, the following references were found within the state of the art of the hydrodeoxygenation process of vegetable oils to produce green or renewable diesel.

US Publ. No. 2004/0230085 relates a process to produce hydrocarbons useful as diesel or as a component thereof, from a feed of biological origin; the process comprises two steps, HDO and isomerization (which is operated at countercurrent). The raw material of biological origin is selected from vegetable oils, animal fats, fish oils, and mixtures of them: castor oil, rapeseed, canola, sunflower, flaxseed, mustard, peanut, olive, palm, castor, coconut, lard, beef tallow, or fat contained in milk. The catalytic system for HDO comprises one or more catalytic beds. The HDO stage is carried out at pressure of 50 to 100 bar, temperature of 300 to 400° C. After the HDO stage, the water has to be removed from the product. The process of this patent includes a pre-hydrogenation stage at hydrogen pressure of 10 to 100 bar, temperature between 150 to 250° C. The prehydrogenation and HDO stage are carried out in the presence of a hydrogenation catalyst containing a group VIII and/or VIB metal, such as Pd, Pt, Ni, NiMo or CoMo supported on alumina and/or silica.

US Publ. No. 2006/0264684 describes a process for producing diesel with cetane number of 100 and low cold properties, which is obtained from biorenewable feedstocks such as vegetable oils. The process includes a pretreatment stage to remove contaminants such as alkali metals from the raw material. Then the HDO stage is performed to obtain a fraction in the diesel range. The isomerization step is carried out if the cold properties of the biofuel are to be improved. The renewable feedstock can be: canola, corn, soybean, fat, tallow oil, containing aliphatic hydrocarbon chains from $C_{10}$ to $C_{20}$, they also include by-products of the wood industry.

These feedstocks may contain contaminants such as: Na, K, P, $H_2O$ and detergents, which are removed, by pretreatment with an ion exchange resin such as Amberlyst-15.

In the second stage of the process, the effluent that comes from the first reaction zone is contacted with a hydrogenation catalyst in the presence of hydrogen in order to hydrogenate the olefinic or unsaturated fraction of aliphatic chains. The hydrogenation catalyst can be Ni or NiMo dispersed in a support material. Other catalysts can be Pt or Pd supported on gamma-alumina. The hydrogenation conditions are a temperature between 200 to 300° C., hydrogen pressure of 500 to 1000 psi, LHSV of 1 to 4 $h^{-1}$. In the presence of an UOP catalysts (NiMo or CoMo) with a continuous flow is used and a temperature of 325° C., hydrogen pressure of 500 psi, and WHSV of 0.8 $h^{-1}$, it is obtained a yield of diesel up to 98% and a HDO yield of soybean oil of 85%. A WHSV of 0.3 $h^{-1}$ allows a HDO increase to 99%, but the yield of diesel is decreased to 90%.

U.S. Pat. No. 8,084,655 refers to an hydrotreating process used to transform a liquid renewable source with aliphatic HC chains from $C_{12}$ to $C_{20}$ such as oils from canola, palm, coconut, sunflower, soybean, algae, and used oil, as well as tallow. This process uses a catalyst with one or more active metals of Ni, Co, Mo, W, and combinations of two or more of them, in concentrations of 0.5 to 10% wt. These metals are supported on a first oxide material, selected from alumina, silica, titania, zirconia, silica-alumina or combinations thereof, with surface area of 100 to 300 $m^2/g$, and a second oxide, such as zeolite in amounts of 25 to 50% wt, which is physically mixed with the active metal and alumina. Zeolite is particularly important for the hydroisomerization and hydrocracking reactions. Zeolites that have 10 to 12 rings such as ZSM-5, Faujasite (USY or Y), ZSM-11, Mordenite and Beta are preferred.

The catalyst is contacted with hydrogen at temperature between 250 and 425° C., a pressure between 500 to 2500 psi, so that the hydrocracking and isomerization reactions produce a paraffinic product. The feedstock can be a vegetable or animal oil that contains one or more triacylglycerides. The catalyst contains Ni in reduced state at concentrations of 45 to 60% wt, and it is reduced with hydrogen at temperature of 100 to 400° C. The zeolite is selected from: ZSM-5, ZSM-11, Faujasite (USY or Y), Mordenite and Beta. The product, green diesel, has a high cetane number. The branching degree obtained by isomerization depends on the operating temperature, the type of zeolite selected, and the combination of metals in the catalyst. Part of the product is recycled into this process, mixing it with hydrogen and fresh raw material.

US Publ. No. 2012/0209017 A1 refers to a hydrotreatment process to obtain biofuel (with less than 1 ppmw of Fe) from the conversion of a renewable source, such as oils from soybean, sunflower, canola, corn, olive, castor, coconut, palm, *Jatropha curcas*, rapeseed, or derivatives of microbial sources; as well as animal fats such as lard, beef tallow, and fish oil. The process consists of two stages: a) hydrotreatment (decarboxylation and decarbonylation reactions) that are carried out in a fixed bed reactor at pressure of 10 to 150 bar, temperature of 200 to 400° C., using a hydrogenation catalyst containing metals of group VIII and/or VIB of the periodic table. As an example, Pt, Pd, Ni, NiMo or CoMo have been used and supported on alumina and/or silica, b) hydroisomerization or isomerization to produce iso-paraffins. In order to improve the cold properties, the product obtained from the hydrotreatment stage is passed to an isomerization stage, where the iso-paraffins are produced. The presence of the following metals: Fe, Na, Ca, Mg, P and C could cause the plugging of the HDT reactor; whereby there is the necessity to dilute the catalyst with quartz sand in a 2:1 ratio.

EP Pat. No. 2540804 refers to a catalyst where one or more metals are selected from the group of Ni, Co, Mo or W or mixtures, the content of the active metal is 0.5 to 60% wt. Whether only Ni is considered, then the content is 25 to 60% wt. The catalyst is in reduced form and the support can be alumina, silica, titania, zirconia, silica-alumina with surface area of 300 $m^2/g$ and combinations thereof, whether the first oxide of the support is not zeolite then a second oxide is a zeolite, selected from ZSM-5, ZSM-11, Faujasite Y or USY, Mordenite and Beta. Optionally a promoter is used as an element of the groups I and II: Sn, Cu, Ag, and Au. The HDO process is carried out at temperature of 250 to 425° C., pressure of 500 to 200 psi, LHSV of 1 to 5 $h^{-1}$. The feedstock can be triacylglycerides with fatty acids of 12 to 20 carbon atoms, including oils from sunflower, *Jatropha curcas*, canola, palm, soy, coconut, castor, as well as poultry fat and tallow.

U.S. Pat. No. 8,530,715 discloses a method comprising the hydrotreating of a feedstock that contains at least one renewable triacylglyceride (TAG), renewable fatty acids, $C_1$ to $C_5$ renewable fatty acid (alkyl ester), and a mixture thereof, in presence of a non-sulfurized hydrotreatment catalyst. In order to produce hydrocarbons with odd number of carbon atoms, cyclic hydrocarbons, hydrocarbons with number of even number of carbon atoms may be used depending on the hydrotreatment temperature. As the temperature increased, the weight ratio of hydrocarbons with even number of carbon atoms to hydrocarbons with odd number of carbon atoms will be less than 1:1.

In this process, at least 58% of the feedstock is converted to other materials.

The process includes the control of hydrotreatment temperature, since the concentration of aromatics in the product increases as temperature increases too. If the temperature of the hydrotreatment is between 150 to 475° C., the weight ratio of hydrocarbons with even carbon atoms to hydrocarbons with odd carbon atoms is larger than 1:1. If the temperature of the hydrotreatment is between 482 to 530° C., the weight ratio is less than 1:1.

U.S. Pat. No. 8,766,025 describes a process for producing fuel from renewable raw materials such as vegetable oils from camelina, palm, *Jatropha curcas*, spent cooking oil and animal fats such as poultry fat. The raw material is pretreated with Amberlyst-15. In the process, the feedstock is hydrogenated and deoxygenated in the first reaction zone, a fraction of the effluent is recycled and the other one is passed through the second reaction zone to obtain a fuel with boiling points in the diesel range. If it is desired, the product obtained from the second reaction zone can be isomerized using an isomerization catalyst to improve the cold properties of the biofuels.

Catalysts such as Ni or NiMo supported on a high surface area support are used for the hydrogenation zone. Another catalysts may contain one or more supported noble metals as Pt and/or Pd in gamma alumina. The experimental conditions include temperature between 200 to 300° C., a pressure between 1379 kPa (200 psi or 14 $kg/cm^2$) to 4826 kPa (700 psi). The mentioned catalysts can also carry out the hydrodeoxygenation reactions (decarbonylation, decarboxylation and deoxygenation) at pressure between 3447 kPa (500 psi) to 6895 kPa (1000 psi), a temperature between 288 to 345° C. and a LHSV from 1 to 4 $h^{-1}$.

US Publ. No. 2015/0266796A1 refers to a new process which includes hydrotreatment of biological oxygenated oils (triacylglycerides) to obtain paraffinic fuels such as jet fuel/diesel, solvents and base oils. The process involves in a first step the hydrotreatment of triacylglycerides to produce long chain paraffins with a narrow boiling range. At the second step, the resulting paraffins are brought into contact with a catalyst to extend the boiling range of paraffins. From this process, a paraffinic product with chains of 2 to 40 carbon atoms is obtained. The process comprises: a) hydrotreatment of oxygenated biological oils to produce a mixture of propane, CO, $CO_2$, water and paraffins, b) recovery of paraffins and, c) conversion of paraffins to obtain a mixture of light and heavy paraffins. A combination of conventional hydrogenation-dehydrogenation catalysts such as $Pt/Al_2O_3$ is used. The biological oxygenated oils can be from canola, sunflower, soy, olive oil, linseed, palm, mustard, castor, peanut, and so on. The hydrogenation-dehydrogenation catalysts contain selected metals as Ni, Fe, Co, Rh, Ru, Os, Pd, Re, Sn, Ge, Ga, In, Pb, Pt; but preferably Pt on alumina, in Pt concentration of 0.1 to 5% wt. The operating conditions are temperature of 300 to 750° F., pressure of 50 to 3000 psi and a LHSV from 0.1 to 5 $h^{-1}$. The isomerization step is carried out at pressure of 15 to 3000 psi, LHSV of 0.1 to 5 $h^{-1}$ and a $H_2$/feed ratio between 0.1 to 30 $ft^3$/bbl. In this publication, an example related with the hydrodeoxigenation and isomerization of canola oil in two reactors in series is mentioned. The first reactor at 600° F. contains a NiMo/alumina catalyst (from Chevron Lummus Global), with a surface area of 180 $m^2$/g, the second reactor operate at 650° F. with a Pt/SAPO-11 catalyst at a pressure of 1000 psi, LHSV 0.35 $h^{-1}$ and $H_2$/feed ratio of 5.0 $ft^3$/bbl. The product composition was analyzed by gas chromatography and the main components were i-$C_{16}$, i-$C_{17}$, and i-$C_{18}$.

Publ. No. WO 2015/181744 discloses a process for obtaining diesel from a renewable raw material such as vegetable oil or animal fat. The raw material is pretreated with ammonia at temperature of 130 to 250° C. and pressure of 1 to 8 MPa, giving a mixture of glycerin and a mixture of fatty acid amides, which are subsequently separated. The mixture of fatty acid amides is hydrotreated in the presence of hydrogen at pressure of 4 to 15 MPa, a LHSV of 1 $h^{-1}$ and a temperature between 250 to 400° C. which allows obtaining CO, $H_2O$, $H_2$, and ammonia in addition to a fraction of diesel (mixture of linear paraffins). The diesel fraction obtained passes to a hydroisomerization stage. The HDT catalyst consists of Ni or Co combined with Mo or W, such as Ni—Mo, Ni—W, Co—W, Co—Mo, supported on alumina, silica, activated carbon, titania or mixtures thereof. The process to convert vegetable oil and animal fats into paraffins consists of a single step, which involves contacting the feed with hydrogen and one catalyst.

The present disclosure exceeds all the above references, because it is intended to provide a process for hydrodeoxygenation of non-edible vegetable oils to produce green diesel, this process consists in contacting the non-edible vegetable oil with a Nickel-Molybdenum catalyst supported in alumina-titania (catalyst IMP-DSD-17 protected in Mexican patents MX 985494 and U.S. Pat. No. 6,383,975 whose ownership is of the Mexican Petroleum Institute), in a fixed bed reactor with the presence of hydrogen. The non-edible vegetable oil can be palm oil, where the triacylglycerides that constitute it are mainly converted into paraffins, carbon dioxide, carbon monoxide, propane and water, through hydrodeoxygenation reactions. Another object of the present disclosure is that it involves the following reactions: hydrogenation, decarboxylation, decarbonylation and/or deoxygenation, which are carried out in a fixed bed reactor at a temperature range of about 270° C. to about 360° C., a pressure of about 40 $kg/cm^2$ to about 60 $kg/cm^2$, a liquid hourly space velocity (LHSV) between about 0.8 $h^{-1}$ to about 3.0 $h^{-1}$, and an $H_2$/oil ratio of about 2700 $ft^3$/bbl to about 7000 $ft^3$/bbl, obtaining a conversion greater than 99%.

DESCRIPTION OF THE DISCLOSURE

The hydrodeoxygenation (HDO) process of non-edible vegetable oils or animal fats described in the present disclosure is useful for obtaining green diesel, also called renewable diesel. This process consists in contacting the vegetable oil with a supported bimetallic catalyst (IMP-DSD-17), as well as with excess $H_2$ in a continuous fixed bed reactor, which under certain reaction conditions (temperature, pressure, and space velocity), it is aimed to favor the selective deoxygenation of the raw material in order to obtain a product or effluent consisting of water, carbon oxides, light hydrocarbons, hydrogen, and liquid hydrocarbons in the range of about $C_8$ to about $C_{24}$. The transformation of triacylglycerides to green diesel or renewable diesel is carried out through reactions of hydrocracking, hydrogenation, deoxygenation, decarboxylation, and decarbonylation.

Raw Material:

The raw material consists of renewable non-edible vegetable oils, consisting of triacylglycerides, diglycerides, monoglycerides and free-fatty acids; such as palm, used cooking oil, *Jatropha curcas*, castor oils, among others. As an example of the present disclosure, the palm oil was selected as raw material, its properties are shown in Table 1.

Catalyst for HDO:

To carry out the hydrodeoxygenation process, it is necessary for the presence of a catalyst to convert the triacylglycerides of vegetable oils to a mixture of hydrocarbons in the boiling range of diesel. High yields of green diesel require catalysts that exhibit high hydrodeoxygenation (HDO) activity to convert the triacylglicerides. The conventional catalysts for HDO contain active metals on alumina with moderate surface area. The best known commercial catalysts consist of molybdenum (Mo) or Tungsten (W) sulfides promoted by Nickel (Ni) or Cobalt (Co), supported on alumina, and with them high yields of diesel fractions are obtained. The supported material comprises any substrate of refractory metal oxide such as alumina, silica, titania, or combinations thereof, which has specific physical and chemical properties. For the present invention, the catalyst selected for the HDO tests of the non-edible vegetable oil is the catalyst IMP-DSD-17, whose holder is the Mexican Petroleum Institute (Patents Nos. MX 985494 and U.S. Pat. No. 6,383,975), which consists of a formulation of Molybdenum promoted by Nickel and Phosphorus as an additive supported on an alumina-titania material.

HDO Process:

Hydrogenation and deoxygenation reactions are carried out in the hydrotreatment process (which in turn involves decarboxylation, decarbonylation and deoxygenation reactions), which remove $O_2$ in the form of $H_2O$ and $CO_x$, producing paraffinic hydrocarbons useful as fuel. The renewable raw materials are acylglycerides and fatty acids, that are currently found in vegetable oils and animal fats. The majority of the acyglycerides will be triacylglycerides but monoacylglycerides and diacylglycerides may also be present, which can also be processed. The breaking of C—O and C—C bonds is carried out in the chemical conversion of the triacylglycerides to obtain paraffins. Likewise, carbon dioxide, carbon monoxide, propane and water are obtained as by-products.

The reactions involved are hydrocracking, hydrogenation, deoxygenation, decarboxylation, and decarbonylation. With this process, a mixture of paraffinic hydrocarbons as valued product is obtained, which can be used individually or mixed with fossil diesel. The catalystic process involves the hydrodesoxygenation of biomass, that is carried out at high temperature and pressure in the presence of a catalytic material, and with an atmosphere of hydrogen in excess. Table 2 shows a summary of the operating condition for the hydrodeoxigenation of liquid biomass reported in the literature, with Nickel-Molybdenum (NiMo) catalysts.

Since the catalyst selected in this invention is a catalyst of NiMo/alumina-titania formulation (IMP-DSD-17) that initially is in the form of an oxide, and therefore inactive, it is necessary to be activated through a sulfuration process, using a mixture of light gas oil (LGO) with Dimethyldisulfide (DMDS), at temperature in a range of about 310° C. to about 330° C., a pressure in a range of about 45 $kg/cm^2$ to about 60 $kg/cm^2$, and an $H_2/HC$ ratio of about 2000 $ft^3/bbl$ to about 3000 $ft^3/bbl$, during a period of about 5 hours to about 10 hours, where the metal oxide state is transformed to the corresponding sulfide, which is the active phase. Once the catalyst is activated and prior to establishing the operating conditions for the hydrodeoxygenation of vegetable oils, a free-DMDS LGO is fed to the reactor for a period of about 40 hours to about 80 hours, after this, the feeding of the vegetable oil, here palm oil, is carried out to start the hydrodeoxygenation process. As an option, the vegetable oil (palm oil) can be mixed with DMDS at a sulfur concentration of 0.1% wt with the purpose of preventing the catalyst deactivation. The main variables for the hydrotreatment of palm oil are: type of catalyst, space velocity, partial pressure of hydrogen, temperature, and hydrogen/oil ratio. The feedstock (vegetable oil) is pre-heated in the range of about 40° C. to about 70° C., after that, the feedstock are entered together with hydrogen into the reactor that operate at a pressure of about 40 $kg/cm^2$ to about 60 $kg/cm^2$, a temperature of about 270° C. to about 380° C., a liquid hourly space velocity of about 0.8 $h^{-1}$ to about 3.0 $h^{-1}$, and an $H_2$/oil ratio of about 2500 $ft^3/bbl$ to about 7000 $ft^3/bbl$. The liquid product obtained from the separator is treated with a nitrogen flow of about 5 L/h to about 10 L/h to remove the hydrogen sulfide traces ($H_2S$; depletion process), in order to obtain a better product quality. When the experimental program considers a change in the operating conditions like temperature, pressure, and/or space velocity; it is recommended that before starting a new balance, a stabilization period of at least about 10 hours is going to be done to establish a steady state condition and thus ensure the reliability of the experimental measures for each balance.

Before finishing each balance, the sampling of the liquid and its experimental analysis is done. The physical and chemical analysis are: total sulfur content (ASTM D-5453), total nitrogen content (ASTM D-4629), specific gravity (ASTM D-1282), atmospheric distillation (ASTM D-86), aromatics content (ASTM D-5186), metals content (e.g. Ca, Mg, Na, and K; EN 14538), phosphorus content (ASTM D-4951), water content (ASTM D-6304), paraffins composition that is determined by gas chromatography with a selective mass detector (GC-MS), calorific value (ASTM D-240), flash point (ASTM D-93), cloud point (ASTM D-2500), and kinematic viscosity at 40° C. (ASTM D-445).

Green Diesel:

The hydrotreatment process of this disclosure has the purpose to produce green diesel, also called renewable diesel, which has the appropriate physical and chemical properties to be used individually or mixed with fossil diesel. In order to clarify, it is necessary to emphasize the difference between biodiesel and green diesel. Biodiesel is defined as a fuel that is composed of monoalkyl esters of long chain fatty acids derived from vegetable oil or animal fats and that complies with ASTM D-6751. Green diesel is defined as a fuel produced from non-fossil renewable resources, including agricultural or forestry plants, animal fats, wastes and wastes generated by the production, processing and marketing of agricultural, forestry and other renewable resources. Green diesel must comply with applicable ASTM specifications for diesel (Reference North Dakota Century Code 57-43.2-01). The biodiesel specifications are in the US ASTM D-6751 standard, some of them are showed in Table 3.

EXAMPLES

Below are some examples for the use of the IMP-DSD-17 catalyst in the hydrodeoxygenation of palm oil in accordance with the present disclosure, it must be well understood that each example is only illustrative, and it is not intended to limit the scope of the invention.

Example 1: NiMo/Alumina-Titania as Catalyst (IMP-DSD-17), Palm Oil as Raw Material 10 mL of the IMP-DSD-17 catalyst (NiMo/alumina-titania) was loaded in a fixed bed reactor at a micro plant scale; the palm oil was feeded into the reactor at up-flow stream. The catalyst was activated in situ using the sulfurization procedure described above. Once the catalyst was activated, the vegetable oil was fed to start the hydrodeoxygenation process; the vegetable oil might be added with DMDS to have a sulfur concentration of 0.1% wt in order to prevent catalyst deactivation. The composition of the palm oil used is shown in Table 4. The palm oil was mixed with hydrogen and fed to the reactor, where the following operating conditions were fixed: pressure of 50 $kg/cm^2$, temperature of 280, 310 and 340° C., LHSV of 1 $h^{-1}$, and $H_2$/oil ratio of 5600 $ft^3/bbl$.

Example 2: CoMoP/Alumina as Commercial Catalyst, Palm Oil as Raw Material

For comparison with the catalyst used in this invention, a commercial catalyst owned by the Mexican Petroleum Institute, IMP-DSD-14+(Mexican Patent MX 198590) with CoMoP/alumina catalytic formulation was tested in the hydrodeoxygenation process, following the activation procedure described above, and using palm oil as raw material. In this example, the palm oil is mixed with hydrogen and fed to the reactor at a pressure of 50 $kg/cm^2$, temperature of 340, 360, and 380° C., LHSV of 1 $h^{-1}$, and $H_2$/oil ratio of 5600 $ft^3/bbl$.

Table 4 shows the results with the NiMo/alumina-titania catalyst (IMP-DSD-17) at temperature of about 280° C. to about 340° C., we observed that the conversion of HDO was greater than 99%, the green diesel yield is greater than 82%, and the paraffin distribution was in the range of $n-C_9$ to $n-C_{18}$, but mostly in the range between $n-C_{15}$ to $n-C_{18}$.

Similar results were obtained with the CoMo catalyst (IMP-DSD-14+) in the temperature range of about 340° C. to about 380° C. The NiMo catalyst (IMP-DSD-17) is considered suitable for this process, because it operates at a lower temperature but the former one gives higher yields on green diesel.

Triacylglycerides are the main components of vegetable oils. The reaction mechanism involved in the conversion of triacylglycerides by hydrodeoxygenation consists of two main stages. In the first stage, the saturation of double bonds occurs and the cracking of triacylglycerides to produce intermediate compounds (diacylglycerides and monoacylglycerides), as well as the formation of propane, and a mixture of carboxylic acids. In the second stage, the carboxylic acids are transformed into paraffins through three different routes: deoxygenation, decarboxylation, and decarbonylation. The products of the first reaction are paraffins and water, the products of the second one are paraffins and $CO_2$, and the products from the latter are paraffins, water and CO. The liquid product is composed of two immiscible phases, water (aqueous phase) and a mixture of hydrocarbons, mainly paraffins (organic phase) constituted by alkanes of 15 to 18 carbon atoms.

Example 3: NiMo Catalyst (IMP-DSD-17), Feedstock: Palm Oil 10 mL of the NiMo/alumina-titania catalyst was loaded into the reactor (fixed bed) at a micro plant scale; the palm oil is fed to the reactor at up-flow. The catalyst is activated in situ using a sulfurization procedure described above.

Once the catalyst is activated, the vegetable oil is fed to start the HDO process; the vegetable oil can be added with DMDS at sulfur concentration of 0.1% p to prevent the catalyst of deactivation. Palm oil is mixed with hydrogen and fed to the reactor that is maintained at a pressure of 50 $kg_f/cm^2$, temperature of about 280° C. to about 340° C., LHSV of 1 $h^{-1}$, $H_2$/oil ratio of 5600 $ft^3$/bbl. The period of the evaluation in the micro plant was 65 days, during this period the main product (green diesel) was recovered and analyzed. The properties obtained are shown in Table 5, a comparison of our results with typical fossil diesel and biodiesel is included.

TABLE 1

Palm oil properties

| Property | Units | Method | Value |
|---|---|---|---|
| Molecular weight | g/mol | Estimated from the composition of fatty acids of the vegetable oil* | 853 |
| Density @ 15.5° C. | kg/m³ | ASTM D-1298 | 913.6 |
| Viscosity @ 40° C. | cSt | ASTM D-445 | 39.48 |
| Flash point | ° C. | ASTM D-97 | 314 |

TABLE 1-continued

Palm oil properties

| | Units | Method | Value |
|---|---|---|---|
| Acid value | mg KOH/g | AOCS Ca 5a-40 | 0.26 |
| Iodine value | g $I_2$/g | AOCS Cd 1-25 | 58.9 |
| Melting point | ° C. | | 15 |
| Cloud point | ° C. | | 3 |
| Ash | % wt | | 0.0013 |
| Fatty acid composition in the palm oil | | | |
| Lauric acid (C12:0) | % wt | AACCI 58-18.01 | 0.12 |
| Myristic acid (C14:0) | | | 0.86 |
| Palmitic acid (C16:0) | | | 39.35 |
| Stearic acid (C18:0) | | | 3.25 |
| Oleic acid (C18:1) | | | 45.38 |
| Linoleic acid (C18:2) | | | 10.51 |
| Arachidic acid (C20:0) | | | 0.53 |

*$M_{aceite} = 3 \sum_{i=1}^{n} w_i MW_i + 39.049$
where $w_i$ is the mass fraction of the i-th fatty acid, MW is the molecular weight of the i-th fatty acid, and the 38.049 figure corresponds to the molecular weight of the CH—C—CH molecular structure present in the triacylgliceride.

TABLE 2

Operating conditions reported in the literature for the HDO of biomass using the Nickel-Molybdenum (NiMo) catalyst.

| Temperature (° C.) | Pressure | LHSV ($h^{-1}$) | $H_2$/HC ratio | Reference |
|---|---|---|---|---|
| 330-398 | 80-140 bar | 0.5-2.5 | 543-890 $Nm^3/m^3$** | [1] |
| 350-370 | 20-40 bar | 1 | 500 $m^3/m^3$ | [2] |
| 275-325 | 500 psi | 0.01-0.0111* | 188 mol/mol | [3] |
| 300-450 | 2-18 MPa | 1-7.6 | 250-1600 $Nm^3/m^3$ | [4] |
| 260-420 | 3.5-18 MPa | — | — | [5] |
| 330 | 1200 psi | 1 | 505.9 L/L | [6] |
| 320 | 3.5 MPa | 1.5 | — | [7] |
| 300-400 | 2-8 MPa | 1-4 | 600 $m^3/m^3$ | [8] |
| 300-400 | 50-80 bar | 1-2 | 1500 NL/L*** | [9] |
| 623 K | 4 MPa | 7.6 | 800 mL/mL | [10] |

*Residence time in the micro-reactor.
**$Nm^3$ = Normal cubic meters.
*** NL = Normal liters

TABLE 3

Biodiesel specifications

| Property | Value | Norm |
|---|---|---|
| Flash point, ° C. | 93 | ASTM D-93 |
| Kinematic viscosity, $mm^2/s$ | 1.9-6.0 | ASTM D-445 |
| Water and sediments, % vol. | 0.050 máx. | ASTM D-2709 |
| Destillation at 90% vol, ° C. | 360 | ASTM D-1160 |
| Density, kg/m³ | 820-845 | — |
| Cetane number | 47 | ASTM D-613 |
| Acid value, mgKOH/g | 0.50 | ASTM D-664 |
| Mono, Di y Tri-acylgliceride, % wt | 0.40 | ASTM D-6584 |
| Metals of group I (Na + K), mg/kg | 5 máx. | EN14538 |
| Metals of group II (Ca + Mg), mg/kg | 5 máx. | EN14538 |
| Phosphorus, % p | 0.001 | ASTM D-4951 |
| Sulfur, ppm | 15 | ASTM D-5453 |

TABLE 4

Hydrodeoxygenation of palm oil

| | Sample 1 | Sample 2 |
|---|---|---|
| Feedstock | Palm oil | Palm oil |
| Catalyst | NiMo/alumina-titania | CoMo/alumina |
| Flow mode | continuous upward flow | continuous upward flow |

TABLE 4-continued

Hydrodeoxygenation of palm oil

| | Sample 1 | | | Sample 2 | | |
|---|---|---|---|---|---|---|
| Pressure, kg/cm² | 50 | | | 50 | | |
| LHSV, h⁻¹ | 1 | | | 1 | | |
| H₂/oil ratio, mol/mol | 41.5 | | | 41.5 | | |
| Temperature, ° C. | 280 | 310 | 340 | 340 | 360 | 380 |
| Product composition | | | | | | |
| H₂O, % wt | 8.4 | 8.3 | 7.6 | 5.2 | 3 | 4.3 |
| CO₂ + CO, % wt | 3.6 | 4.2 | 4.7 | 1.5 | 1.5 | 1.8 |
| Propane, % wt | 1.6 | 1.5 | 1.4 | 0.6 | 0.5 | 0.6 |
| Sulfur, ppm | 60 | 25 | 12 | 14 | 4.2 | 3.3 |
| Total nitrogen, ppmw | 5.2 | 1.2 | <0.3 | 1.3 | 0.9 | 0.5 |
| HDO, % | >99 | >99 | >99 | >99 | >99 | >99 |
| Green diesel yield, % | 87 | 82.7 | 84 | 89.9 | 92.7 | 90 |
| Paraffin distribution, % wt | | | | | | |
| n-C₁₅ | 14.5 | 16.5 | 17 | 10.8 | 14.5 | 14.7 |
| n-C₁₆ | 21.9 | 20.9 | 20.7 | 29 | 26.6 | 28.2 |
| n-C₁₇ | 23.9 | 27.8 | 28.1 | 15.8 | 18.4 | 16 |
| n-C₁₈ | 39.7 | 34.8 | 34.1 | 39.3 | 30.5 | 26.6 |

TABLE 5

Physical and chemical properties of Green diesel, fossil diesel, and biodiesel

| Property | Green diesel (1) | Fossil diesel (2) | Biodiesel (3) |
|---|---|---|---|
| Higher heating value, MJ/kg | 43.47 | 42.34 | 41.3 |
| Flash point, ° C. | 138 | 104 | 174 |
| Cloud point, ° C. | 21 | 3 | 16 |
| Kinematic viscosity at 40° C., mm²/s | 3.94 | 3.81 | 4.5 |
| Specific gravity at 20/4° C. | 0.7781 | 0.8414 | 0.855 |
| Sulfur, mg/kg | 3.2 | 303 | N.R.(4) |
| Nitrogen, mg/kg | <0.3 | 62 | N.R.(4) |
| Aromatics content, % vol | 0.6 | 22.4 | N.R.(4) |
| Olefins, % vol | 0.3 | 9.6 | N.R.(4) |
| Saturated compounds, % vol | 99.1 | 68 | N.R.(4) |
| Distillation profile, ° C. (ASTM D-86) | | | |
| IBP | 276.9 | 226.8 | N.R.(4) |
| At 5% vol | 284.4 | 252.8 | N.R.(4) |
| At 10% vol | 285.7 | 262.7 | N.R.(4) |
| At 20% vol | 287 | 276.4 | N.R.(4) |
| At 30% vol | 288.3 | 285.5 | N.R.(4) |
| At 40% vol | 289.8 | 294.8 | N.R.(4) |
| At 50% vol | 291.4 | 302.6 | N.R.(4) |
| At 60% vol | 293.3 | 311 | N.R.(4) |
| At 70% vol | 295.5 | 320.1 | N.R.(4) |
| At 80% vol | 298.4 | 331.4 | N.R.(4) |
| At 90% vol | 302.3 | 347.5 | N.R.(4) |
| At 95% vol | 306.3 | 362.6 | N.R.(4) |
| FBP | 320 | 362.9 | N.R.(4) |

(1) Green diesel obtained in the present invention.
(2) Fossil diesel from a Mexican refinery (U-700-2 plant)
(3) Nagi et al. 2008. Palm Biodiesel an Alternative Energy for the Energy Demands of the future. ICCBT F(07) pp. 79-94.
(4)Not reported by Nagi et al. (2008).
IBP = Initial boiling point.
FBP = Final boiling point.

REFERENCES

[1] Stella Bezergianni. Catalytic Hydroprocessing of Liquid Biomass for Biofuels Production (Chapter 9). Liquid, Gaseous and Solid Biofuels—Conversion Techniques, Prof. Zhen Fang (Ed.), ISBN: 978-953-51-1050-7, InTech, DOI: 10.5772/52649. Mar. 20, 2013. http://dx.doi.org/10.5772/52649.

[2] Sándor Kovacs, Tamás Kasza, Artur Thernesz, Ilona Wálhné Horváth, Jeno Hancsók. Fuel production by hydrotreating of triglycerides on NiMo/Al₂O₃/F catalyst. Chemical Engineering Journal 2011; 176-177:237-243.

[3] Lalita Attanatho. Performances and Kinetic Studies of Hydrotreating of Bio-Oils in Microreactor. Ph. D. Thesis. Oregon State University. Aug. 6, 2012.

[4] Rogelio Sotelo-Boyás, Fernando Trejo-Zárraga and Felipe de Jesús Hernández-Loyo. Hydroconversion of Triglycerides into Green Liquid Fuels (Chapter 8). Hydrogenation. Iyad Karamé (Ed.), ISBN 978-953-51-0785-9, InTech, DOI: 10.5772/3208338. Oct. 10, 2012. http://dx.doi.org/10.5772/48710.

[5] Edward Furimsky. Hydroprocessing challenges in biofuels production, Review. Catalysis Today 2013; 217:13-56.

[6] Stella Bezergianni, Athanasios Dimitriadis, Loukia P. Chrysikou. Quality and sustainability comparison of one- vs. two-step catalytic hydroprocessing of waste cooking oil. Fuel 2014; 118:300-307.

[7] Jefferson Roberto Gomes, Julio Amílcar Ramos Cabral, Andrea De Rezende Pinho, Luis Fernando Soares de Azevedo. Process for producing light olefins from a feed containing triglycerides. United States Patent US 20090326293 A1. Dec. 31, 2009.

[8] Masita Mohammada, Thushara Kandaramath Hari, Zahira Yaakob, Yogesh Chandra Sharma, Kamaruzzaman Sopian. Overview on the production of paraffin based-biofuels via catalytic hydrodeoxygenation. Renewable and Sustainable Energy Reviews 2013; 22:121-132.

[9] A. K. Sinha, M. Anand, B. S. Rana, R. Kumar, S. A. Farooqui, M. G. Sibi, R. Kumar, R. K. Joshi. Development of Hydroprocessing Route to ransportation Fuels from Non-Edible Plant-Oils. Catal Sury Asia 2013; 17:1-13. DOI:10.1007/s10563-012-9148-x.

[10] Yanyong Liu, Rogelio Sotelo-Boya's, Kazuhisa Murata, Tomoaki Minowa, and Kinya Sakanishi. Hydrotreatment of *Jatropha curcas* Oil to Produce Green Diesel Over Trifunctional Ni—Mo/SiO₂—Al₂O₃Catalyst. Chemistry Letters. 2009; 38(6):552-553. DOI: 10.1246/cl.2009.552.

The invention claimed is:

1. A hydrodeoxygenation process, comprising:
activating a catalyst, the catalyst selected from a group consisting of Nickel-Molybdenum supported on alumina-titania, or Cobalt-Molybdenum supported on alumina, wherein activating the catalyst comprises a sulfuration process at a temperature range of about 310° C. to about 330° C., a pressure in a range of about 45 kg/cm² to about 60 kgf/cm² for a period of about five hours to ten hours; and
a reaction between one of vegetable oils or animal fats with hydrogen, the reaction in the presence of the activated catalyst;
wherein the reaction is loaded in a fixed bed reactor; and
wherein the process results in a green diesel yield greater than 82% and a conversion rate greater than 99%.

2. The process according to claim 1, wherein the reaction breaks the C—O bonds present in triacylglycerides of the vegetable oils or animal fats in order to obtain diaclyglycerides, monoacylglycerides, and carboxylic acids.

3. The process according to claim 2, wherein the carboxylic acids are transformed into paraffins, carbon dioxide, carbon monoxide, and water through chemical reactions of deoxygenation, decarboxylation, and decarbonylation.

4. The process according to claim 3, wherein the chemical reactions of deoxygenation, decarboxylation, and decarbonylation occur in the following order: first deoxygenation, followed by decarboxylation, and finally decarbonylation.

5. The process according to claim 1, wherein the fixed bed reactor has a temperature in a range of 270° C. to 360° C.

6. The process according to claim 1, wherein the fixed bed reactor has a medium pressure in a range of 40 kgf/cm$^2$ to 60 kgf/cm$^2$.

7. The process according to claim 1, wherein the fixed bed reactor has a liquid hourly space velocity (LHSV) in a range of about 0.8 h$^{-1}$ to 3.0 h$^{-1}$.

8. The process according to claim 1, wherein the fixed bed reactor has a hydrogen/oil ration in a range of about 2,500 ft$^3$/bbl to 7,000 ft$^3$/bbl.

9. The process according to claim 1, wherein the catalyst has a compact density in a range of about 0.5 g/cm$^3$ to about 1 g/cm$^3$, a fracture resistance in a range of about 2 lbf/mm to 8 lbf/mm, a surface area in a range of about 100 m$^2$/g to about 200 m$^2$/g, a pore volume in a range of about 0.1 cm$^3$/g to about 1 cm$^3$/g, a Molybdenum content in a range of about 1% wt to about 20% wt, a Nickel content in a range of about 1% wt to about 10% wt, and a Titanium content in a range of about 1% wt to about 10% wt.

10. The process according to claim 1, wherein the process results in a green diesel yield greater than 92%.

11. The process according to claim 1, wherein triacylglycerides of the vegetable oils or animal fats are converted to green diesel (mixture of paraffins) by hydrocracking, saturation, and deoxygenation reactions.

12. The process according to claim 10, wherein the green diesel has a density in a range of 0.75 g/cm$^3$ to 0.85 g/cm$^3$, a kinematic viscosity in a range of 2 cSt to 4 cSt, a higher heating value in a range of 40 MJ/kg to 50 MJ/kg, and a cloud point range between about 15° C. to 20° C.

13. The process according to claim 10, wherein the green diesel has a density of 0.77 g/cm$^3$, a kinematic viscosity of 3 cSt, and a higher heating value of 46 MJ/kg.

14. The process according to claim 10, wherein the green diesel has a concentration of total sulfur of less than about 5 ppmw, and a total nitrogen concentration of less than about 5 ppmw.

15. The process according to claim 10, wherein the paraffins are in the range of 8 to 24 carbon atoms (n-$C_8$ to n-$C_{22}$).

16. The process according to claim 10, wherein the green diesel has aromatic compounds in concentrations less than 5% vol, and olefinic compounds in concentrations less than 5% vol.

17. The process according to claim 1, wherein activating the catalyst further comprises bringing the catalyst into contact with a primary light gas oil (LGO) doped with dimethyldisulfide (DMDS), under a hydrogen atmosphere for about 8 to 23 hours.

18. The process according to claim 10, wherein the paraffins are in the range of 15 to 18 carbon atoms (n-$C_{15}$ to n-$C_{18}$).

19. The process according to claim 1, wherein the vegetable oils or animal fats are transformed into paraffinic hydrocarbons with a carbon range of naphtha, kerosene, or diesel.

* * * * *